US00PP34665P2

(12) United States Plant Patent
Courtney et al.

(10) Patent No.: US PP34,665 P2
(45) Date of Patent: Oct. 18, 2022

(54) ***EUTROCHIUM* PLANT NAMED 'JOJO'**

(50) Latin Name: *Eutrochium fistulosum*
Varietal Denomination: JoJo

(71) Applicant: Kind Earth Growers LLC, Ottsville, PA (US)

(72) Inventors: John Mark Courtney, Upper Black Eddy, PA (US); Joseph Henry LaMent, Kintnersville, PA (US)

(73) Assignee: KIND EARTH GROWERS LLC, Ottsville, PA (US)

( * ) Notice: Subject to any disclaimer, the term of this patent is extended or adjusted under 35 U.S.C. 154(b) by 0 days.

(21) Appl. No.: 17/574,426

(22) Filed: Jan. 12, 2022

(51) Int. Cl.
*A01H 5/02* (2018.01)
*A01H 6/14* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Penny J. Aguirre

(57) ABSTRACT

A new cultivar of *Eutrochium* plant named 'JoJo' that is characterized by its double sterile flowers that are vibrant pink in color, its upright and relatively compact plant habit, its mature stems that are dark maroon in color, and its free flowering blooming habit.

2 Drawing Sheets

Botanical classification: *Eutrochium fistulosum.*
Variety denomination: 'JoJo'.

BACKGROUND OF THE INVENTION

The present invention relates to a new and distinct cultivar of *Eutrochium fistulosum* and will be referred to hereafter by its cultivar name, 'JoJo'. 'JoJo' is a new herbaceous perennial suitable for landscape plantings.

'JoJo' was discovered by the Inventors as a chance seedling in a container in Ottsville, Pa. in September of 2017. It was found in a block of containers planted with unnamed and unpatented plants of *Eutrochium fistulosum.*

The new cultivar was first asexually propagated by stem cuttings by one of the Inventors in Ottsville, Pa. in spring of 2018. Asexual propagation by stem cuttings has determined that the characteristics of this cultivar are stable and are reproduced true to type in successive generations.

SUMMARY OF THE INVENTION

The following traits have been repeatedly observed and represent the characteristics of the new *Eutrochium*. These attributes in combination distinguish 'JoJo' as a unique cultivar of *Eutrochium.*

1. 'JoJo' exhibits double sterile flowers that are vibrant pink in color.
2. 'JoJo' exhibits an upright and relatively compact plant habit.
3. 'JoJo' exhibits mature stems that are dark maroon in color.
4. 'JoJo' exhibits a free flowering blooming habit.

The plants of *Eutrochium fistulosum* growing in the containers surrounding the claimed plant (likely parent plants) are all similar to 'JoJo' in having flowers that are pink in color, whorled lanceolate leaves, leaves with serrate margins, and upright hollow stems. The likely parent plants of 'JoJo' all differ from 'JoJo' in having single flowers that are fertile, and less vibrant pink in color, taller plant heights, less compact plant habits, and mature stems that are green-maroon in color. 'JoJo' can be most closely compared to *Eutrochium fistulosum* 'Bartered Bride' (not patented). 'Bartered Bride' is similar to 'JoJo' in having whorled lanceolate leaves, leaves with serrate margins, and upright hollow stems. 'Bartered Bride' differs from 'JoJo' in having single flowers that are fertile and white in color and a taller plant height.

BRIEF DESCRIPTION OF THE DRAWINGS

The accompanying color photographs illustrate the overall appearance and distinct characteristics of a 3-year-old plant of the new *Eutrochium* as grown outdoors in 5-gallon containers in Ottsville, Pa.

The photograph in FIG. 1 provides a view of the plant habit of 'JoJo' in bloom.

Figure 1:
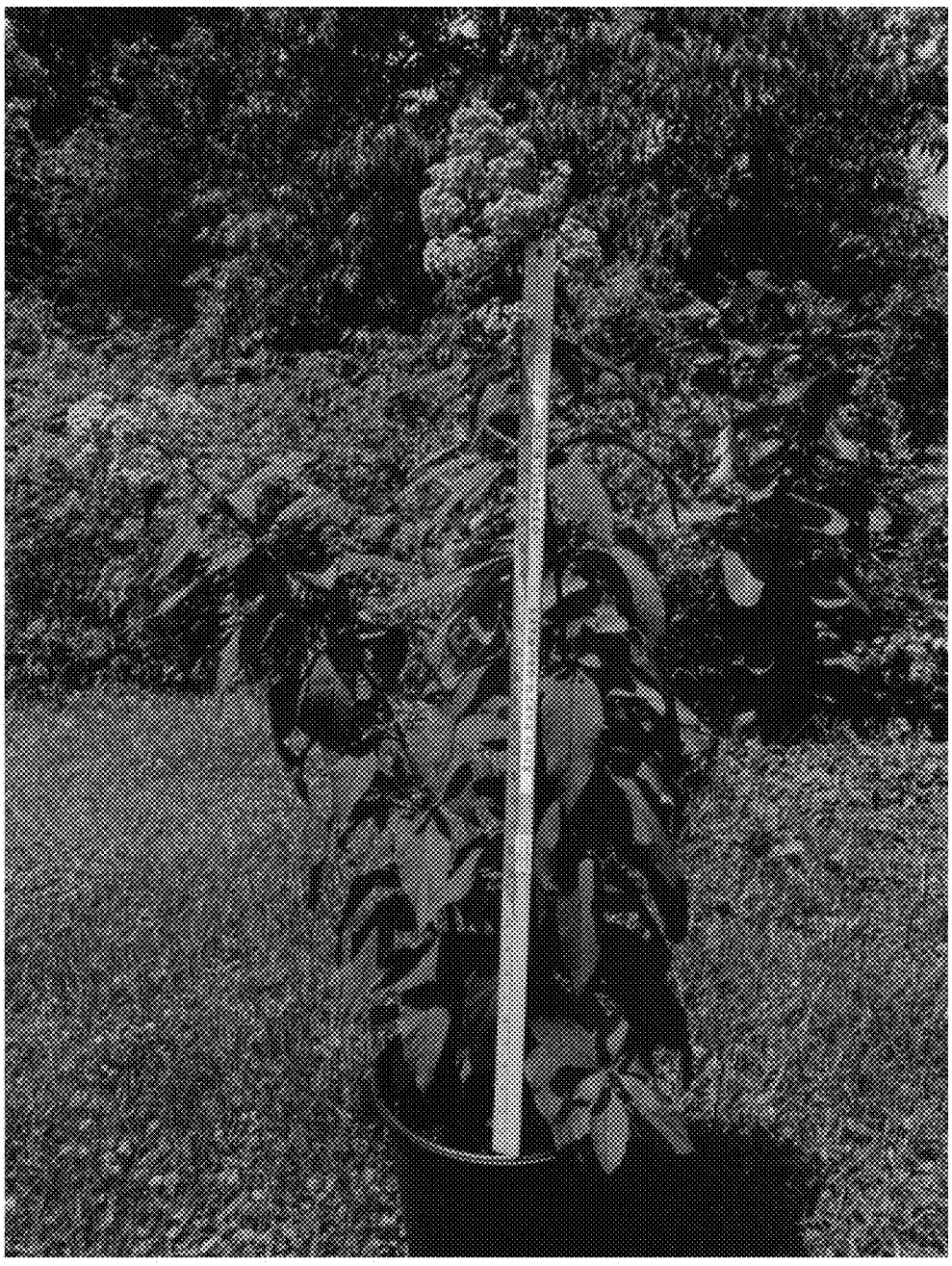
Figure 2:
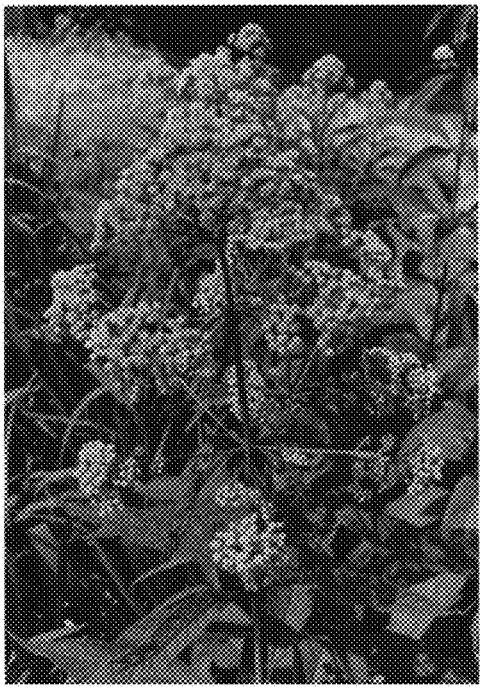

The photograph in FIG. 2 provides a close-up view of an inflorescence of 'JoJo'.

Figure 3:
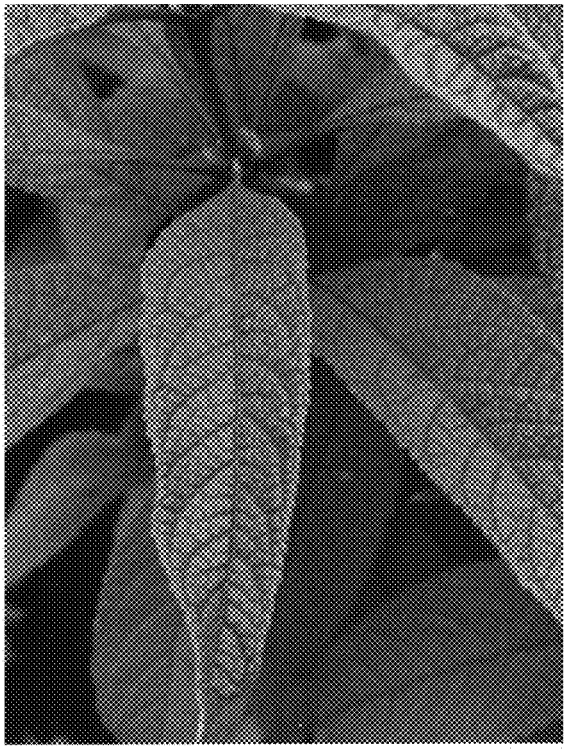

The photograph in FIG. 3 provides a close-up view of the foliage of 'JoJo'.

The colors in the photographs are as close as possible with digital photography techniques available, the color values cited in the detailed botanical description accurately describe the colors of the new *Eutrochium.*

DETAILED BOTANICAL DESCRIPTION

The following is a description of 3-year-old plants of the new cultivar as grown outdoors in 5-gallon containers outdoors in Ottsville, Pa. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming season.*—4 to 6 weeks in late summer in Pennsylvania.

*Plant type.*—Herbaceous perennial.

*Plant habit.*—Upright, relatively compact.

*Height and spread.*—An average of 51 cm in height, 18 cm in width as a 3-year-old plant in a container and reaches an average of 91 to 1.2 m in height and spread when grown in the landscape.

*Hardiness.*—At least in U.S.D.A. Zones 4 to 8.

*Diseases and pests.*—No susceptibility or resistance to diseases or pests has been observed.

*Root description.*—Fibrous, thin, NN155B in color.

*Propagation.*—Stem cuttings.

*Growth rate.*—Moderately vigorous.

*Root development.*—Time required for root initiation is 3 weeks, time required to produce a young plant from a rooted cutting is 4 to 6 weeks.

Stem description:

*Branching habit.*—Basal branches.

*Internode length.*—Average of 3.5 cm.

*Stem surface.*—Young stems; moderately covered with short pubescent hairs that match the surface color, 0.5 mm in length, all stems covered with minute lenticels; average of 0.5 mm in length, up to 15 per 1 cm, 200A in color, older stems; glabrous, slightly glossy.

*Stem size.*—An average of 30 cm in length (to base of primary peduncle) and 6 mm in width.

*Stem color.*—Young stems: 145B, mature stems: flushed with 180A.

Foliage description:

*Leaf division.*—Simple.

*Leaf shape.*—Lanceolate-elliptic.

*Leaf base.*—Cuneate.

*Leaf apex.*—Acuminate.

*Leaf margin.*—Serrate.

*Leaf venation.*—Pinnate, only conspicuous on main vein lower surface, colors on both surfaces match surface color with main vein on lower surface 196B and becomes flushed with 183A.

*Leaf attachment.*—Petiolate.

*Leaf arrangement.*—Variable, primarily whorls or alternate.

*Leaf number.*—Average of 18 per stem.

*Leaf surface.*—Dull and glabrous on upper and lower surface.

*Leaf color.*—Young and mature upper surface 137A and 144A, young and mature a lower surface; 138A.

*Leaf size (fully expanded).*—Average of 9 cm in length and 3.5 cm in width when mature.

Inflorescence description:

*Inflorescence type.*—Cymose panicle of composite inflorescences comprised of disk florets only.

*Inflorescence size.*—Cymose panicle; an average of 26 cm in height and 18 cm in width, composite; an average of 5 cm in length and 7 cm in width.

*Inflorescence number.*—1 panicle per stem, an average of 5 cymes per panicle, an average of 50 composite inflorescences per cyme.

*Peduncles.*—Round in shape, strong, held vertical, primary peduncle an average of 22 cm in length and 4 mm in width, secondary peduncles (on cymes) an average of 15 cm in length and 3 mm in width, tertiary peduncles an average of 2 cm in length and 1 mm in width, surface; moderately covered with short pubescent hairs that match the surface color, 0.5 mm in length, covered with minute lenticels; average of 0.5 mm in length, up to 15 per 1 cm, 200A in color, surface color; 145B and flushed with 180A.

*Pedicels.*—Round in shape, an average of 6 mm in length, 1 mm in diameter, strong, 182B in color, surface is matte and densely covered with short stiff pubescent hairs that match surface color and 0.3 mm in length.

*Inflorescence buds.*—Oblong in shape, 3 mm in depth and 2 mm in diameter.

*Flower fragrance.*—None.

*Persistence of flowers.*—Persistent.

*Lastingness of inflorescence.*—About 3 weeks.

Involucral bracts:

*Bract number.*—Average of 12.

*Bract arrangement.*—Imbricate.

*Bract size.*—An average of 4 mm in length and 1.5 mm in width.

*Bract color.*—Young and mature, inner and outer surface 76D.

*Bract texture.*—Both surfaces glabrous and shiny.

*Bract apex.*—Acute.

*Bract base.*—Cuneate to attenuate.

*Bract margins.*—Entire.

*Bract shape.*—Lanceolate to linear.

Disk florets (perfect):

*Number.*—About 12.

*Shape.*—Tubular, corolla is fused.

*Size.*—About 4 mm in length and 1 mm in width.

*Color.*—Young inner and outer surface; 77C, mature inner and outer surface; 77A.

*Receptacle.*—Conical, about 2 mm in height and width, 137C in color.

*Phyllaries.*—Numerous, very fine, an average of 4 mm in length, 76D.

Reproductive organs:

*Pistils.*—1, stigma; linear, about 2 mm in length and <1 mm in diameter, 76D in color, style; about 8 mm in length, 76D in color, ovary superior; <1 mm in width and 2 mm in length, lanceolate in shape, 7D in color.

*Stamens.*—About 4, filaments; 4 mm in length, 76D in color, anthers; 1 mm in length, about 200B in color, pollen; none observed.

*Fruit and seed.*—Not observed to date.

It is claimed:

1. A new and distinct cultivar of *Eutrochium* plant named 'JoJo' as described and illustrated herein.

* * * * *